United States Patent [19]
Kilbourn et al.

[11] 3,966,947
[45] June 29, 1976

[54] PYRIDYL PHENYL-CARBAMATE RODENTICIDE

[75] Inventors: Edward E. Kilbourn, Chalfont; Ernest D. Weiler, Ambler, both of Pa.

[73] Assignee: Rohm and Haas Company, Philadelphia, Pa.

[22] Filed: Oct. 3, 1975

[21] Appl. No.: 619,278

Related U.S. Application Data

[62] Division of Ser. No. 429,464, Dec. 28, 1973, Pat. No. 3,929,808.

[52] U.S. Cl............. 424/263; 260/294.8 G; 260/270 PY
[51] Int. Cl.²............................ A01N 9/22
[58] Field of Search............ 260/294.8 G, 270 PY; 424/263

[56] References Cited

UNITED STATES PATENTS

| | | | |
|---|---|---|---|
| 3,284,461 | 11/1966 | Wibert et al. | 260/295 CA |
| 3,428,642 | 2/1969 | Debay et al. | 260/295 CA |
| 3,676,457 | 7/1972 | Hubele et al. | 260/471 |

OTHER PUBLICATIONS

Novokov et al., Chem. Abstracts, vol. 70, (17) 77,728 W (Apr., 1969).

*Primary Examiner*—Alan L. Rotman

[57] ABSTRACT

3-Pyridylmethyl N-(4'-substitutedmercaptophenyl) carbamates and their acid salts and metal salt complexes useful as a rodenticide.

8 Claims, No Drawings

PYRIDYL PHENYL-CARBAMATE RODENTICIDE

This is a division of application Ser. No. 429,464 filed Dec. 28, 1973, now U.S. Pat. No. 3,929,808.

The present invention relates to 3-pyridylmethyl N-(4'-mercaptophenyl)carbamate and its mercapto derivatives and more particularly to their use and of compositions containing them for the control and extermination of pest rodents. This includes their salts and complexes.

The common rat, *Rattus norvegicus*, is vicious and constantly poses a serious threat to the health and well being of man. Rats and mice are destructive animals and a serious nuisance, causing millions of dollars damage annually to farms, agronomic crops, homes, food processing plants and many other businesses. Rats bite at least 14,000 (possibly up to 60,000) people every year, according to the U.S. Public Health Service, and are known carriers of over 35 contagious diseases including bubonic plague, trichinosis, typhus, rat bite fever, amoebic dysentery, tuberculosis, infectious jaundice and rabies. During the years from 1898 to 1923, almost 11 million deaths were caused by rat-borne plagues.

Use of rodenticides, fumigants, sprays and traps are the primary methods employed for the control of pest rodents. The term "pest rodents" refers not only to members of the order Rodentia but also to those of lagomorpha, which cause health hazards or economic loss unless kept in check. Rodenticides may be used in the form of a tracking powder or a bait or may be applied as a spray on the rodent's natural foodstuffs. The rodenticides used as a bait are of two classes: single- and multi-dose. Multi-dose rodenticides are usually selected over a single-dose rodenticides, as they have been safer in the past than the available single-dose rodenticides. The multi-dose rodenticides are anti-coagulants, including a number of different 4-hydroxy-coumarin and 1,3-indandione compounds. These multi-dose rodenticides consumed in small daily amounts have a lethal effect on rats and mice after liver stores of vitamin K have been depleted. Anti-coagulants are less effective on mice than rats, as mice are considered to be nibblers and may not consume an adequate amount of treated bait to have a lethal effect. A single-dose rodenticide which would be relatively safe to the person handling the material and to non-target species of animals and yet effective on a variety of pest rodents is highly desirable.

Many compounds are toxic to rodents. However, very few of these compounds are anywhere near suitable for use as a rodenticide because it is necessary for the pest rodent to consume voluntarily a sufficient amount of the poison even though sufficient untreated food may also be available. In bait rodenticides, feed acceptance is the key to excellence, and in all rodenticides safety and efficacy are highly important.

The 3-pyridylmethyl N-(4'-mercaptophenyl)carbamate and its derivatives of the present invention are so highly toxic to a wide variety of pest rodents that a single dose is sufficient; yet they are relatively safe for use in the presence of other species which may inadvertently ingest limited quantities of the rodenticide. Furthermore, rats and other pest rodents willingly consume the compounds in sufficiently lethal amounts when present in baits. Alternatively the compounds may be employed in compositions to be sprayed on natural foodstuffs. They may also be employed in a tracking powder, especially for use against mice, which habitually clean their paws by licking.

The basic compounds of the present invention have the formula:

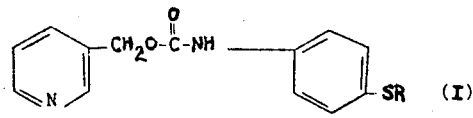

wherein R is
a. hydrogen,
b. alkyl of 1 to 5 carbon atoms,
c. allyl,
d. CN
e. $CCl_3$ and
f. 5-tetrazolyl The preferred compounds are those wherein R is alkyl of 1 to 4 carbon atoms.

The compounds may be prepared by permitting equimolar amounts of 4-RS phenyl isocyanate and 3-pyridylcarbinol to react in the presence of an inert solvent, e.g., pyridine, an aromatic hydrocarbon or acetonitrile, in accordance with the following equation:

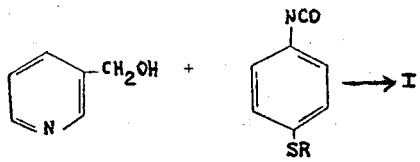

3-Pyridylcarbinol is a product of commerce. The RS-substituted phenyl isocyanates may be readily made by standard procedures.

The following typical examples describe variations in the preparation of 3-pyridylmethyl N-(4'-mercaptophenyl)carbamate and its various derivatives.

EXAMPLE 1

Preparation of 3-pyridylmethyl N-(4'-mercaptophenyl)carbamate p-Mercaptophenyl isocyanate (0.9g., 0.00595 mole) was added to a solution of 3-pyridyl carbinol (0.65g., 0.00595 mole) in 50 ml. of benzene and the reaction mixture was allowed to stand over the weekend. It was then heated to reflux to assure completion of the reaction and then cooled to give a white solid. This was isolated as 1.2g. and was a 78% yield of 3-pyridylmethyl N-(4'-mercaptophenyl)carbamate.

EXAMPLE 2

Preparation of 3-pyridylmethyl N-(4'-methylthiophenyl)carbamate

To a solution of 4.4g. (0.04 mole) of 3-pyridyl carbinol in 50 ml. of benzene containing 0.1g. of Dabco catalyst was added, dropwise, a solution of 6.6g. (0.04 mole) of p-methylthiophenyl isocyanate (New Haven Chemicals) in 50 ml. of benzene. During the addition of white solid separated and the temperature rose from 23°C. to 34°C. The mixture was stirred at ambient temperature for 16 hrs. and the product was filtered off. After oven-drying in vacuo there was obtained 10.4g. melting at 133° – 135°C. This is a 95% yield of 3-pyridylmethyl N-(4'-methylthiophenyl)carbamate.

EXAMPLE 11

Preparation of 3-pyridylmethyl N-(4'-thiocyanophenyl)carbamate

To a solution of p-thiocyanophenyl isocyanate (5.25g., 0.0298 mole) in 100 ml. of benzene was added 3-pyridyl carbinol (3.25g., 0.0298 mole). An immediate exothermic reaction took place and a solid precipitated. After standing over the weekend 5.5g. of solid was isolated and after recrystallization from toluene this gave 4.0g. melting at 188°–191°C. This was a 47% yield of 3-pyridylmethyl N-(4'-thiocyanophenyl)carbamate.

EXAMPLE 13

Preparation of 3-pyridylmethyl N-(4'-(5-tetrazolylmercaptophenyl)carbamate

A reaction mixture consisting of 3-pyridylmethyl N-(4'-thiocyanophenyl)carbamate (2.85g., 0.01 mole), sodium azide (0.65g., 0.01 mole) and 50 ml. of topped dimethylformamide was heated to reflux 2 hrs., then, after standing over the weekend was similarly heated another 2 hrs. then concentrated in vacuo. The residual oil was slurried in 100 ml. of water, acidified to pH 2 with 12N HCl and filtered. The residue was recrystallized from isopropanol to yield 0.6g. of recrystalized solid melting at 188°–194°C with decomposition. This is an 18% yield of 3-pyridylmethyl N-(4'-(5-tetrazolylmercaptophenyl)carbamate.

Also included in the compounds of this invention are the acid addition salts and metal salt complexes of 3-pyridylmethyl N-(4'-mercaptophenyl)carbamate and its 4'-substituted-mercapto derivatives. These also are excellent rodenticides.

The 3-pyridylmethyl N-(4'-substituted-mercaptophenyl)carbamates can form novel acid salts with a strong inorganic or organic acid. Typical strong acids include hydrobromic, hydrochloric, hydrofluoric, nitric, phosphoric, sulfuric, chloroacetic, oxalic, maleic, succinic and p-toluenesulfonic.

The novel metal salt complexes may be depicted by the structure

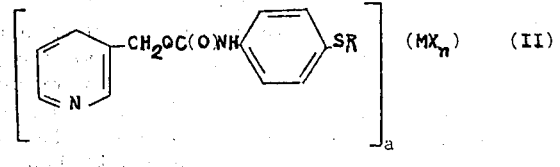

wherein R has the meanings defined above, M is a cation of a metal such as cadmium, calcium, cobaltous, cupric, ferrous, ferric, manganous, mercuric, nickel, silver, stannous and zinc, X is an anion forming a compound with the cation M in which the compound has sufficient solubility to form a complex with the compounds of the invention such as bromide, chloride, iodide, perchlorate, carbonate, bicarbonate, nitrate, phosphate, sulfate, bisulfate, acetate, maleate, oxalate and p-toluenesulfonate, a is an integer corresponding to the valence of cation M and n is an integer which for the anion X satisfies the valence of the cation M.

The preparation of 3-pyridylmethyl N-(4'-methylthiophenyl)carbamate hydrochloride is typical of these acid salts. Gaseous HCl was passed into a solution of 5g. of 3-pyridylmethyl N-(4'-nitrophenyl)carbamate in 100 ml. of acetone. A solid formed and after filtration, washing and drying in a vacuum oven this amounted to 5.0g. of solid. This was found by analysis to contain 44.45% C, 3.48% H, 11.55% N and 21.54% Br; calculated for $C_{13}H_{11}N_3O_4 \cdot HBr$ is 44.09% C, 3.42% H, 11.86% N and 22.56% Br. The product is an 88% yield of 3-pyridylmethyl N-(4'-methylthiophenyl)carbamate hydrochloride.

A typical preparation for a metal salt complex of the compounds of the invention is as follows. To a solution of 5.0g. (0.0183 mole) of 3-pyridylmethyl N-(4'-methylthiophenyl)carbamate in 300 ml. of methanol was added a solution of 1.2g. (0.0091 mole) of anhydrous $ZnCl_2$ in 20 ml. of methanol. The resulting precipitate was isolated by filtration and drying to give 5.3g. of solid melting at 209°–211°C. The product was an 83% yield of 3-pyridylmethyl N-(4'-methylthiophenyl)carbamate-zinc chloride complex.

The following Tables I and II give physical constants for the intermediate phenyl isocyanates and for typical novel carbamates of this invention.

Table I

| 4-RSC$_6$H$_4$NCO | | Intermediates |
| Used in Example | —SR = | Boiling Point °C/Pressure mm. |
|---|---|---|
| 1 | —SH | 56–61/0.85 |
| 2 | —SCH$_3$ | a commercial product |
| 3 | —SC$_2$H$_5$ | 67–72/0.25 |
| 4 | —SC$_3$H$_7$-n | 90–95/0.4 |
| 5 | —SC$_3$H$_7$-iso | 65–79/0.3 |
| 6 | —SC$_4$H$_9$-n | 105–109/0.35 |
| 7 | —SC$_4$H$_9$-iso | 110/0.25 |
| 8 | —SC$_4$H$_9$-sec | 78–82/0.25 |
| 9 | —SC$_6$H$_{13}$-n | 104–124/0.25 |
| 10 | —S allyl | 77–81/0.1 |
| 11 | —SCN | brown oil* |
| 12 | —SCCL$_3$ | brown oil* |

*Identified by the infrared spectrum

Table II

Typical 3-Pyridylmethyl N-(4'-RS-phenyl)carbamate

| Example | R= | Melting Point (°C) | Empirical Formula | Analysis* C | H | N |
|---|---|---|---|---|---|---|
| 1 | H | 166–169.5 | C$_{13}$H$_{12}$N$_2$O$_2$S | 59.8(60.0) | 4.3(4.6) | 10.5(10.8) |
| 2 | CH$_3$ | 133–135 | C$_{14}$H$_{14}$N$_2$O$_2$S | 61.31(61.3) | 5.0(5.1) | 10.2(10.2) |
| 3 | C$_2$H$_5$ | 116–119 | C$_{15}$H$_{16}$N$_2$O$_2$S | 62.5(62.3) | 5.6(5.5) | 9.4(9.7) |
| 4 | n-C$_3$H$_7$ | 124–126 | C$_{16}$H$_{18}$N$_2$O$_2$S | 63.3(63.6) | 6.1(6.0) | 9.1(9.3) |
| 5 | iso-C$_3$H$_7$ | 103–107 | C$_{16}$H$_{18}$N$_2$O$_2$S | 63.7(63.6) | 6.0(6.0) | 9.5(9.3) |
| 6 | n-C$_4$H$_9$ | 115–117 | C$_{17}$H$_{20}$N$_2$O$_2$S | 64.5(64.5) | 6.4(6.4) | 8.8(8.9) |
| 7 | iso-C$_4$H$_9$ | 100–104 | C$_{17}$H$_{20}$N$_2$O$_2$S | 64.7(64.5) | 6.4(6.4) | 8.8(8.9) |
| 8 | sec-C$_4$H$_9$ | 113–115 | C$_{17}$H$_{20}$N$_2$O$_2$S | 64.4(64.5) | 6.4(6.4) | 8.9(8.9) |
| 9 | n-C$_6$H$_{13}$ | 96.5–102 | C$_{19}$H$_{24}$N$_2$O$_2$S | 65.7(66.3) | 7.1(7.0) | 8.4(8.1) |
| 10 | allyl | 96–99 | C$_{16}$H$_{16}$N$_2$O$_2$S | 5.4(5.4) 63.8(64.0) | 9.2(9.3) | |
| 11 | CN | 188–191 | C$_{14}$H$_{11}$N$_3$O$_2$S | 58.9(58.9) | 3.8(3.9) | 14.5(14.7) |

Table II-continued

Typical 3-Pyridylmethyl N-(4'-RS-phenyl)carbamate

| Example | R= | Melting Point (°C) | Empirical Formula | Analysis* C | H | N |
|---|---|---|---|---|---|---|
| 12 | CCl₃ | 153–155(dec.) | $C_{14}H_{11}Cl_3N_2O_2S$ | 44.8(44.5) | 3.1(2.9) | 7.4(7.4) |
| 13 | 5-tetrazolyl | 188–194(dec.) | $C_{14}H_{12}N_6O_2S$ | 51.3(51.2) | 3.7(3.7) | 24.7(25.6) |
| 14 | HCl salt of Example 2 | 193–195(dec.) | $C_{14}H_{14}N_2O_2S$ · HCl | 54.3(54.1) | 5.2(4.9) | 8.8(9.0) |
| 15 | Oxalic acid salt of Example 2 | 209–211(dec.) | $C_{14}H_{14}N_2O_2S$ ·(—COOH)₂ | 52.9(52.7) | 4.5(4.4) | 7.6(7.7) |
| 16 | Zinc chloride complex of Example 2 | 154–156 (dec.) | $C_{14}H_{14}N_2O_2S$ · ½ $ZnCl_2$ | 49.2(49.1) | 4.3(4.1) | 8.1(8.2) |

*The number in parenthesis represents the theoretical value as calculated from the empirical formula The 3-pyridylmethyl N-(4'-mercaptophenyl)carbamate and its 4'-substituted mercapto derivatives and salts and complexes of the present invention may be formulated into rodenticidal compositions such as baits, tracking powders, and sprays. A bait comprises a semi-moist or dry edible carrier and the toxicant. The dry carrier is generally preferred and may be a combination of natural food products such as whole ground corn, steel cut oats, sugar, molasses, rice, vegetable oil, salt, dehydrated fruit, fish meal, tankage or wheat. When necessary to use in damp locations, the matrix may be a water repellent material such as paraffin wax or an acrylic polymer.

The compounds of the present invention may be incorporated as a toxicant in bait formulations, either alone or in combination with other toxicants. When used as the sole toxicant in baits, the compounds of the present invention may be used in any rodenticidally effective concentration.

Depending on the susceptibility of the rodents to the toxicant and the amount of formulated bait generally consumed, concentrations as low as 0.1%, and especially when intended for mice, even lower than 0.5% may be employed. A typical bait may contain between about 0.5% and 1.5% of the toxicant by weight. Surprisingly it has been found that there is no upper limit to the amount of compound which may be present in a bait; hence, the bait can contain from 0.1 to 100% of the toxicant. Rats, mice and other rodents accept the compounds of the present invention so well that even when offered free choice between untreated basal ration and a bait consisting entirely of it, they ingest rodenticidally sufficient quantities of the toxicant. An example below describes the formulation of a suitable bait, although wide variations in formulation for different conditions of use are of course expected.

Bait Formulation

A 3-pyridylmethyl N-(4'-substituted-mercaptophenyl)carbamate was blended with the basal ration of a Waring laboratory blender to form 50 grams of a homogeneous premix. The amount of compound utilized was determined by the percentage of active material desired in the feed. The formula for the basal ration is shown below, all percentages being by weight:

| Crude ground corn | 65% |
|---|---|
| Steel cut oats | 25% |
| Powdered sugar | 5% |
| Corn oil | 5% |

The 50 grams of premix containing the toxicant were then mixed with an additional 450 grams of basal ration. These components were mixed in a Little Ford Lodige mixer for three minutes.

Tracking powders, which are particularly effective against mice, may be either a compound of the present invention in finely powdered form or a mixture of the compound with powdered carrier, e.g., talc, sugar, milk powder, Indian corn meal, fish meal, cornstarch, flour, and bentonite, or the like, or any combination thereof which tends to induce the animals contaminated with the preparation to lick themselves more thoroughly. In tracking powders, a compound of the present invention may be incorporated in amounts from 100% down to 0.1% by weight with proper formulation. An example below describes the preparation of a suitable tracking powder.

Tracking Powder

The active compound is finely pulverized by mortar and pestle to form a 100% active tracking powder. To form a 5% active material, it may be mixed with 10X confectioner's sugar in a 1 to 19 ratio and at other ratios for other levels of active compound.

The compounds were preliminarily evaluated for their ability to kill albino rats (*Rattus norvegicus*) by oral administration to two rats at a dosage of 50 mg./kg. In the standard test the effect on the rats is observed over a 14 day period. Table III gives the results with typical examples of this invention.

Table III

| Example | Preliminary Rodenticidal Activity Acute oral toxicity (50 mg./kg.) rats dead/rats in test | |
|---|---|---|
| 1 | 2/2 | (within 8 days) |
| 2 | 2/2 | (with 4 hours) |
| 3 | 2/2 | (within 8 days) |
| 4 | 2/2 | (within 24 hours) |
| 5 | 2/2 | (within 24 hours) |
| 6 | 2/2 | (within 8 days) |
| 7 | 2/2 | (within 8 days) |
| 8 | 2/2 | (within 8 days) |
| 9 | 0/2 | (at 100 mg./kg.) |
| 10 | 2/2 | (within 24 hours) |
| 11 | 2/2 | (within 24 hours) |
| 12 | 2/2 | (within 8 days) |
| 13 | 2/2 | (within 8 days) |
| 14 | 2/2 | (within 3 hours) |
| 15 | 2/2 | (within 3 hours) |
| 16 | 2/2 | (within 3 hours) |

One of the most significant secondary tests is a standard one known as the paired-preference test. In this test the rodents are given a free choice between the treated and untreated bait in individual cages or in a communal tank. Such a test most nearly approximates practical use conditions.

When caged individually, they were provided with dual feed cups and separate water devices. When caged in a communal tank, they were offered a multiplicity of feed cups and water devices. The basal ration was offered in excess of daily feed requirements in each of two feeders; one treated with the test compound and one without. For each test, equal numbers of each sex were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

To meet the criteria for a single-dose product, a rodenticide in this initial test must kill 75% of the rats within 8 days, where the poison bait is available for the first 72 hours of this period.

The results of representative paired preference tests with several dosage levels on individually caged rodents are given in Table IV.

Another secondary testing procedure is known as the tracking test. In this test the rodents are permitted to walk over areas on which the tracking powder has been placed. One such procedure follows:

Mouse Tracking Test

Feral mice (*Mus musculus*) were each placed in a double cage system for these evaluations. The two cages of each system were connected by a tunnel. The tracking powder or toxicant was placed in the connecting tunnel and on entry pans. Feed and water were provided ad libitum, the water in one compartment of the cage and the feed in the other. An effective single-dose compound will kill 90% of the mice within 8 days, of which they are exposed during the first 72 hours.

The results of representative mouse tracking tests with 3-pyridylmethyl N-(4'-methylthiophenyl)carbamate are shown in Table V.

Table V

Tracking Test Using Feral Mice

| Compound in Tracking Powder | Mice killed within 8 days /Mice in test |
|---|---|
| 10% | 4/4 |
| 5% | 4/4 |
| 2.5% | 4/4 |
| 1.25% | 4/4 |

Table IV

Paired-Preference Test of 3-Pyridylmethyl N-(4'-methylthiophenyl)carbamate Using Individually Caged Rodents

| Rodent Species | | Compound in Basal Ration (parts per millions) | Rodents killed in 8 days/Rodents in test |
|---|---|---|---|
| a) | albino rat | 100,000 | 4/4 |
| | | 50,000 | 2/2 |
| | | 10,000 | 4/4 |
| | | 3,000 | 4/4 |
| | | 1,000 | 4/4 |
| | | 500 | 4/4 |
| | | 300 | 4/4 |
| | | 100 | 2/4 |
| | | 50 | 0/4 |
| b) | Norway rat | 100,000 | 4/4 |
| | | 10,000 | 4/4 |
| | | 5,000 | 4/4 |
| | | 2,500 | 19/20 |
| | | 2,500 | 4/4 |
| | | 1,250 | 4/4 |
| | | 625 | 3/4 |
| | | 2,500* | 20/20* |
| c) | roof rat (*Rattus rattus*) | 100,000 | 4/4 |
| | | 10,000 | 4/4 |
| | | 5,000 | 3/4 |
| | | 2,500 | 4/4 |
| | | 2,500 | 19/20 |
| | | 1,250 | 3/4 |
| | | 625 | 2/4 |
| | | 312 | 0/4 |
| d) | feral mice (*Mus musculus*) | 100,000 | 4/4 |
| | | 10,000 | 4/4 |
| | | 5,000 | 4/4 |
| | | 2,500 | 4/4 |
| | | 1,250 | 3/4 |
| | | 625 | 2/4 |
| | | 312 | 4/4 |
| | | 156 | 4/4 |
| | | 75 | 0/4 |
| e) | deer mice (*Peromyscus* spp.) | 100,000 | 4/4 |
| | | 10,000 | 4/4 |
| | | 5,000 | 4/4 |
| | | 2,500 | 4/4 |
| | | 2,500 | 19/20 |
| | | 1,250 | 3/4 |
| | | 625 | 1/4 |
| | | 312 | 0/4 |
| f) | ground moles (*Microtus* spp.) | 2,500 | 2/2 |
| | | 2,500 | 18/20 |
| | | 1,250 | 2/2 |

*In communal tank

Table V-continued

| Tracking Test Using Feral Mice | |
|---|---|
| Compound in Tracking Powder | Mice killed within 8 days /Mice in test |
| 0.625% | 4/4 |
| 0.312% | 4/4 |
| 0.156% | 1/4 |

We claim:
1. A metal salt complex having the structure

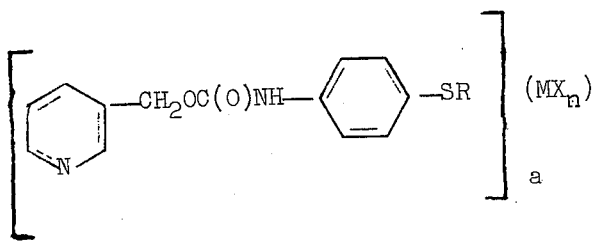

wherein
R is
a. hydrogen
b. alkyl of 1 to 5 carbon atoms
c. allyl
d. CN
e. $CCl_3$ and
f. 5-tetrazolyl M is a metal cation, X is an anion forming a compound with the cation M in which the compound has sufficient solubility to form a metal salt complex, and $a$ is an integer corresponding to the valence of cation M and $n$ is an integer which for the anion X satisfied the valence of the cation M.

2. A metal salt complex according to claim 1 where R is alkyl of 1 to 5 carbon atoms.

3. A metal salt complex according to claim 2 where R is methyl.

4. A metal salt complex according to claim 1 wherein $(MX_n)$ is zinc chloride.

5. A metal salt complex according to claim 4 wherein R is alkyl of 1 to 5 carbon atoms.

6. A metal salt complex according to claim 5 where R is Methyl.

7. A rodenticidal composition comprising a rodenticidally effective amount of a metal salt complex according to claim 1 and an edible carrier.

8. A method of exterminating pest rodents which comprises placing a rodenticidally-effective amount of a metal salt complex of claim 1 in the vicinity of a population of pest rodents in a place where the composition may be easily reached and ingested by the rodents.

* * * * *